United States Patent
Nelson

(10) Patent No.: US 6,875,189 B1
(45) Date of Patent: Apr. 5, 2005

(54) CERVICAL TRACTION DEVICE

(76) Inventor: David Eugene Nelson, 60 Fern Ct., Babbitt, MN (US) 55706

( * ) Notice: Subject to any disclaimer, the term of this patent is extended or adjusted under 35 U.S.C. 154(b) by 0 days.

(21) Appl. No.: 10/770,229

(22) Filed: Feb. 3, 2004

(51) Int. Cl.[7] ................................................ A61F 5/00
(52) U.S. Cl. .......................... 602/17; 602/18; 128/857; 128/DIG. 23
(58) Field of Search .............................. 602/17, 18, 32, 602/74; 128/845, 857, 869, 97.1, DIG. 23; 2/410, 171; 5/636, 637

(56) References Cited

U.S. PATENT DOCUMENTS

| | | | |
|---|---|---|---|
| 4,182,322 A | * | 1/1980 | Miller .......................... 5/637 |
| 5,086,757 A | * | 2/1992 | Lestini ........................ 602/17 |
| 5,109,835 A | | 5/1992 | McDonald |
| 5,195,947 A | * | 3/1993 | Bode ........................... 602/18 |
| 5,314,404 A | * | 5/1994 | Boughner et al. ............. 602/17 |
| 5,697,894 A | * | 12/1997 | Gullichsen et al. ........... 602/32 |
| 5,697,895 A | * | 12/1997 | Bremer ................. 128/DIG. 23 |
| 5,916,185 A | * | 6/1999 | Chitwood ..................... 602/18 |
| 6,468,240 B1 | | 10/2002 | Saunders |
| 6,659,972 B2 | * | 12/2003 | Stamper et al. ............... 602/17 |

* cited by examiner

Primary Examiner—Fadi H. Dahbour

(57) ABSTRACT

An improved cervical traction device having main bodies (12) having at their anterior, inferior ends an occipital support (14) and at their anterior, superior ends a head support (16). Maxillary strap (17) and skull strap (19), located at the inferior ends of main bodies (12), along with forehead strap (18), located at the superior ends of main bodies (12), secure the device to the user. A guide rod (20) is located both inferiorly and superiorly to connect the main bodies (12) along with an adjusting rod (22) which is equidistantly located between guide rods (20). A compression spring (24) is secured around the perimeter of each guide rod (20). An adjusting knob (38) is secured to one end of adjusting rod (22), lateral to main body (12). A securing pin (36) and a support guide (34) allow for easy adjustment of head support (16). A strap (26) and a hook (30) allow the device to be attached to a force application device. A hinge (32) secures occipital support (14) to main body.

2 Claims, 4 Drawing Sheets

CERVICAL TRACTION DEVICE

FEDERALLY SPONSORED RESEARCH

Not Applicable.

SEQUENCE LISTING OR PROGRAM

Not Applicable.

BACKGROUND—FIELD OF INVENTION

This invention relates to cervical spine traction, specifically to an improved mechanism for securing the head allowing for application of a traction force through the spine, for therapeutic benefit.

BACKGROUND—DISCUSSION OF PRIOR ART

The application of a force through the spine, to produce a separation, or longitudinal traction, of vertebrae for therapeutic treatment of pathological conditions, has been utilized for many years. Over time, attempts have been made to isolate this force through cervical and upper thoracic vertebrae, including the use of various harness and pulley type mechanisms. Attempts have also been made to allow individual persons to perform this treatment force independently, without the need for regular assistance from a medical professional. Although many devices have been developed for this purpose, limitations of these devices render them unable to achieve the maximum treatment effect possible, as described here within.

Devices as described in U.S. Pat. No. 4,582,050(1986), U.S. Pat. No. 4,538,598(1985), U.S. Pat. No. 5,024,214 (1991), U.S. Pat. No. 4,971,043(1990), U.S. Pat. No. 4,869, 240(1989), U.S. Pat. No. 5,135,537(1992), U.S. Pat. No. 5,010,880(1991), U.S. Pat. No. 6,045,522(2000), U.S. Pat. No. 5,451,202(1995), U.S. Pat. No. 5,403,266(1995), Des. Pat. No. 344,135(1994), U.S. Pat. No. 5,507,718(1996), U.S. Pat. No. 5,724,993(1998), U.S. Pat. No. 5,823,982 (1998), U.S. Pat. No. 5,752,927(1998), U.S. Pat. No. 6,258, 050(2001), U.S. Pat. No. 6,447,468 B1(2002) apply a force either fully or partially through the jaw to achieve the desired effect in the cervical spine. This application of force through the jaw results in significant forces through the temporomandibular joint, causing significant discomfort to the user. This user discomfort can diminish the treatment effectiveness through increased cervical spine muscle tension, which resists the applied force, and/or inability to tolerate an optimal force application due to pain. Force applied through the jaw can also result in damage to the temporomandibular joint, and thus, cause further pathology and problems for the user.

Some devices have attempted to eliminate the forces applied through the jaw by directing force through the occipital region. U.S. Pat. No. 5,957,976(1999), U.S. Pat. No. 6,113,563(2000), U.S. Pat. No. 5,181,904(1993), Des. Pat. No. 330,083(1992), U.S. Pat. No. 5,067,483(1991), U.S. Pat. No. 4,805,603(1989), U.S. Pat. No. 4,508,109 (1985), Pat. No. Re 32,791(1988), U.S. Pat. No. 4,784,122 (1988), U.S. Pat. No. 4,736,736(1988), U.S. Pat. No. 4,606, 333(1986), U.S. Pat. No. 4,593,684(1986), U.S. Pat. No. 6,468,240 B1(2002), U.S. Pat. No. 6,171,273 BT(2001), U.S. Pat. No. 6,506,174 B1 (2003) deliver a force through the occipital region but are designed to do so in a supine position. These devices have no means to adequately secure themselves in a seated position, and are thus, difficult or impossible to use for a person unable to tolerate a supine position. Similar devices as described in U.S. Pat. Nos. 5,441,479(1995), 6,217,538 B1(2001), 5,454,781(1995), 5,709,649(1998), 5,916,185(1999), 5,569,175(1996) are inadequate in that they do not allow for a sufficient ability to change the cervical spine flexion/extension angle to achieve the desired effect.

U.S. Pat. No. 4,508,109(1985) is designed to be utilized with conventional traction tables which are used in a clinical setting. This device is thus not designed for portable, home use and would require external assistance for application and use.

U.S. Pat. No. 6,517,506 B1(2003) attempts to apply a force to the occipital region in a seated position but does not have a posterior directed force means by which to secure the device. This results in excessive extension positioning being required to keep the device in position, resulting in poor cervical spine positioning and diminished traction force effect for longitudinal traction.

U.S. Pat. Nos. 6,500,136 B2(2002), 4,250,874(1981), 5,713,841(1998), 5,382,226(1995), 5,569,176(1996) are designed to apply an anterior/posterior and/or angular traction force but are unable to apply a longitudinal traction force, which is the desired effect of the present invention.

U.S. Pat. No. 4,407,274(1983) has an inadequate means for securing the traction device, as the described harness would be unable to remain secured to the user with typical traction type forces being applied due to the harness not having a substantial anchoring means to the user. This device is also unable to apply a direct stretch to suboccipital musculature.

U.S. Pat. Nos. 4,987,886(1991) and 5,109,835(1992) attempt to apply force through the occipital area to get the desired traction effect. This design falls short in that either excessive cervical extension would occur, or much of the force would be directed to anterior/posterior traction instead of longitudinal traction, dependent on the angle of the force applied to the device. Lack of a posterior securing member applying an anterior force would also make application of the device independently by the user difficult, as the device would tend to fall anterior and inferior during setup. This device also makes controlling the angle of force difficult, and is unable to achieve a stretch to the suboccipital musculature through upper cervical spine flexion.

U.S. Pat. No. 4,489,715(1984) is designed for use by medical personnel for patient transport and specialized testing. This device is not designed for, and would be both impractical and inappropriate for, delivering a therapeutic traction force to the cervical spine by an individual independently.

BACKGROUND—OBJECTS AND ADVANTAGES

Accordingly, several objects and advantages of my invention are:

a) to provide a cervical traction device which eliminates pressure to the temporomandibular joint during cervical traction application in various positions, including an upright position.

b) to provide a cervical traction device which is portable and thus able to be applied in a nonclinical setting.

c) to provide a cervical traction device which can be easily applied by an individual on themselves without external assistance.

d) to provide a cervical traction device which can apply a direct stretch to suboccipital musculature if desired when a force is applied.

e) to provide a cervical traction device which can allow for cervical spine positioning in various angles and positions as desired during administration of the traction force.

f) to provide a cervical traction device which can allow for a longitudinal traction force to be applied without resultant anterior/posterior traction forces occurring in the cervical spine.

g) to provide a cervical traction device which is fully adjustable to accommodate various sizes and shapes of users.

Still further objects and advantages will become apparent from a consideration of the ensuing description and drawings.

SUMMARY

In accordance with the present invention, a cervical traction device comprises a main body, an occipital support, a head support, a means for securing the device to the user, and a means for attaching the device to a force application device.

DRAWINGS

Drawing Figures

In the drawings, closely related figures have the same number but different alphabetic suffixes.

REFERENCE NUMERALS IN DRAWINGS

12 Main Body
14 Occipital Support
16 Head Support
17 Maxillary Strap
18 Forehead Strap
19 Skull Strap
20 Guide Rod
22 Adjusting Rod
24 Compression Spring
26 Strap
28 Securing Means
30 Hook
32 Hinge
34 Head Support Guide
36 Securing Pin
38 Adjusting Knob

DETAILED DESCRIPTION

Description—FIGS. 1–4-Preferred Embodiment

A preferred embodiment of the cervical traction device is illustrated in FIG. 1 through FIG. 4.

Figure 1:
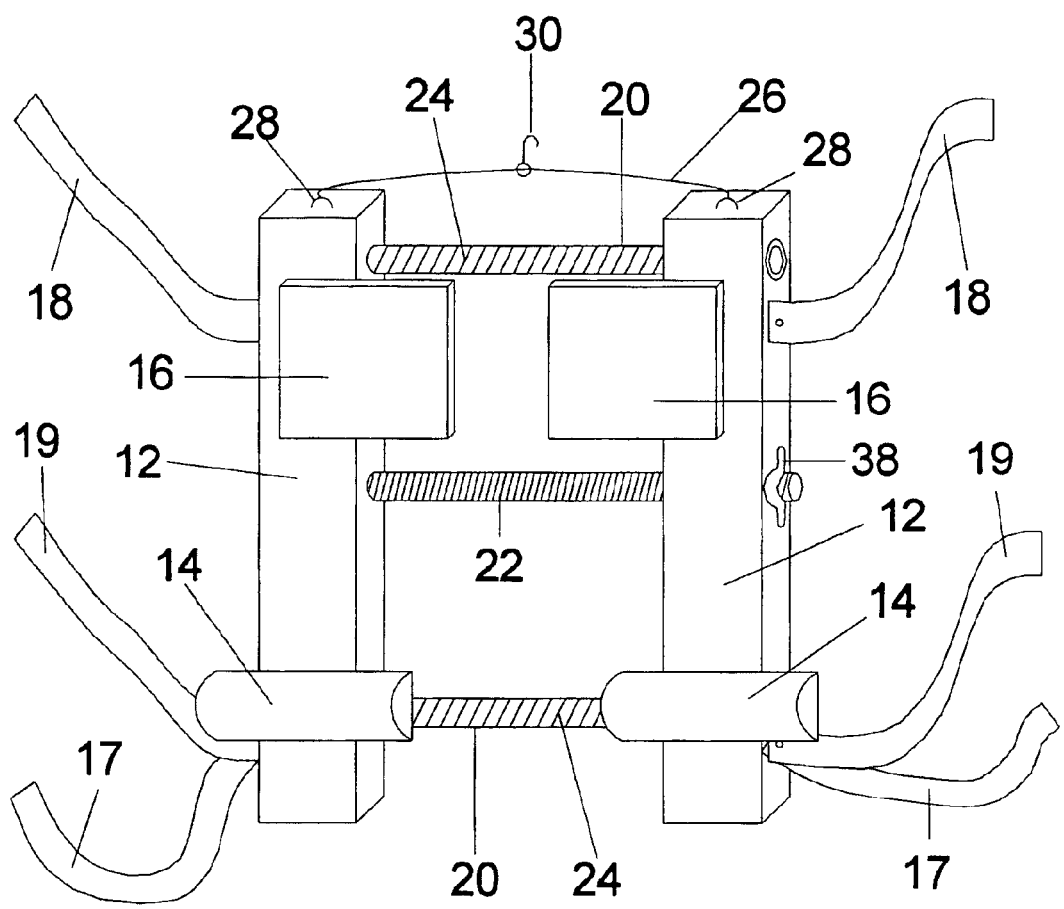
FIG. 1 illustrates an anterior view of my cervical traction device.
Figure 2:
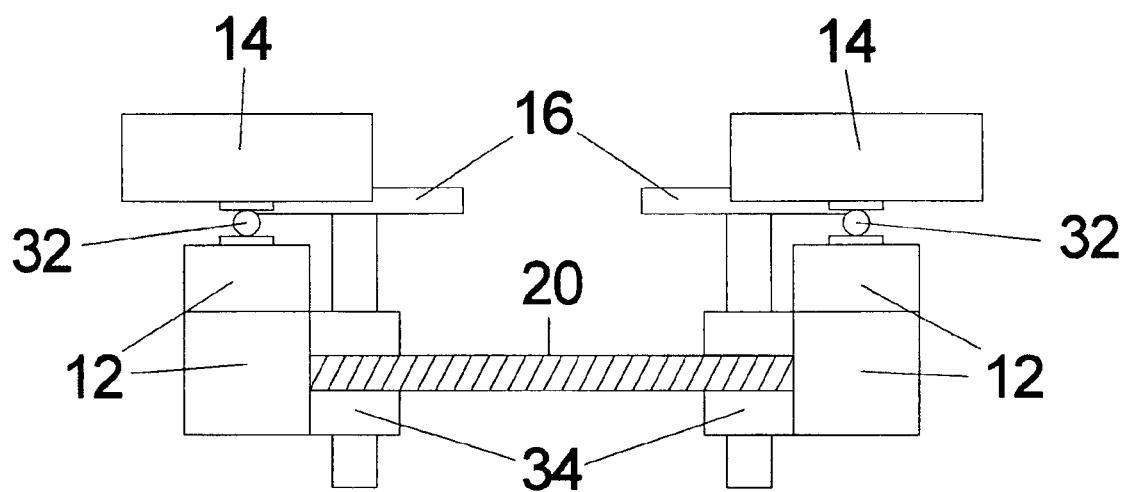
FIG. 2 illustrates an inferior view of my cervical traction device.
Figure 3:
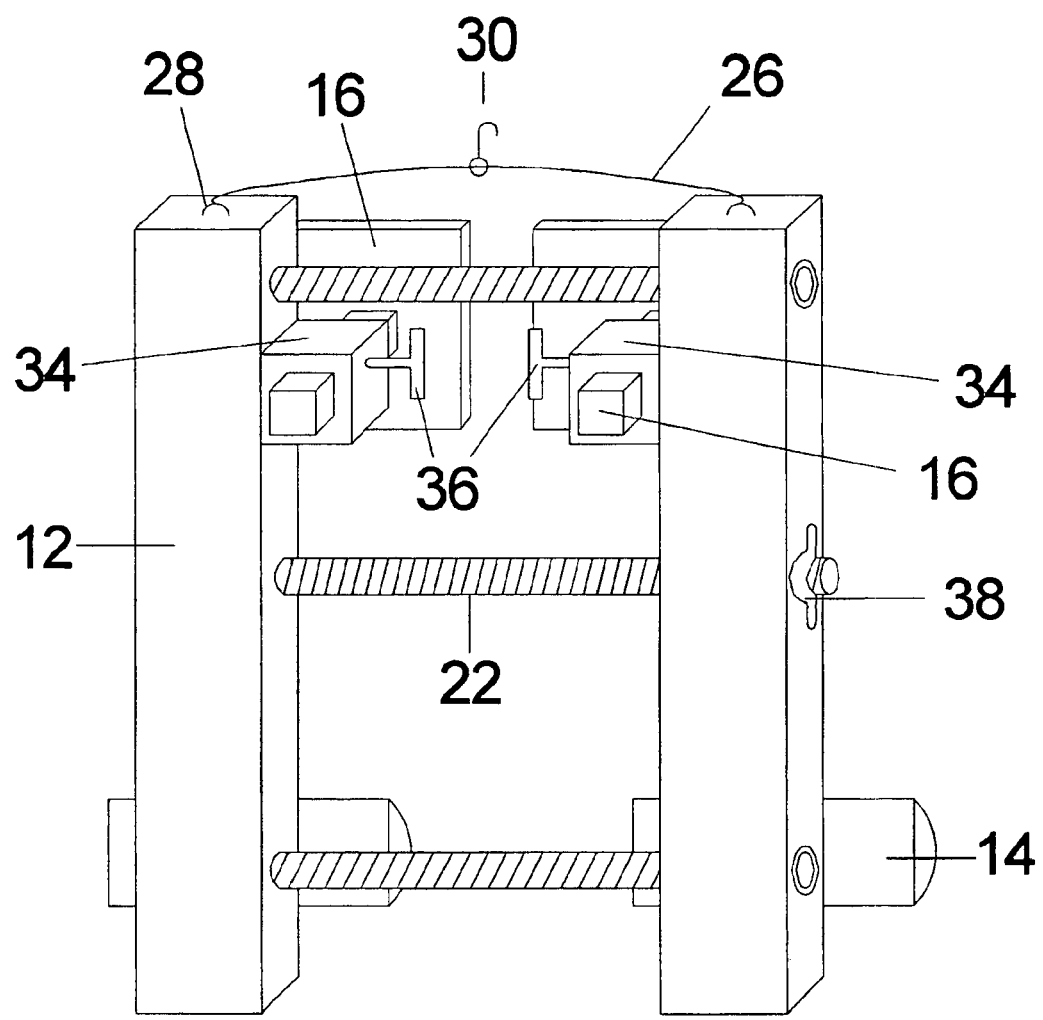
FIG. 3 illustrates a posterior view of my cervical traction device.

FIG. 1 illustrates an anterior view of my cervical traction device. The traction device includes two main bodies 12 which have at their anterior and inferior ends an occipital support 14 and at their anterior and superior ends a head support 16. A maxillary strap 17 and a skull strap 19 are located at the inferior end of main bodies 12, laterally. A forehead strap 18 is located at the superior end of main bodies 12, laterally. Main bodies 12 are connected by a guide rod 20, both superiorly and inferiorly, and an adjusting rod 22, which is equidistantly located between guide rods 20. Guide rods 20 have a compression spring 24 secured around their perimeter, respectively. A strap 26 is secured at the superior ends of main bodies 12 by a securing means 28. A hook 30 is attached to strap 26 at its midpoint and attached to a conventional force application device (not shown). FIG. 2 illustrates an inferior view of my cervical traction device. A hinge 32 secures occipital support 14 to main body 12 with hinge 32 having its axis in a vertical orientation. FIG. 3 illustrates a posterior view of my cervical traction device. Head support 16 has a posterior portion which passes through a head support guide 34. A securing pin 36 passes through head support guide 34 allowing it to contact the posterior portion of head support 16. Also illustrated in FIG. 3 is an adjusting knob 38, which is secured to one end of adjusting rod 22, lateral to main body 12.

Operation—FIGS. 1–4—Preferred Embodiment

In the preferred embodiment of present invention, the cervical traction device would first be adjusted so as occipital supports 14 would contact the user in the area of the posterior and lateral suboccipital protuberance, base of the skull, bilaterally. This would be accomplished by rotating adjusting knob 38 in a clockwise or counterclockwise direction to thus move main bodies 12 either closer together or further apart as needed. Compression springs 24 would apply force laterally in both directions against main bodies 12, thus allowing for good alignment of main bodies 12 and proper positioning of both occipital supports 14 and head supports 16.

Head supports 16 would then be adjusted, dependent upon the desired position and effect, in an anterior or posterior direction. The posterior portion of head support 16 slides through head support guide 34 in an anterior or posterior direction. When the desired position of head support 16 is achieved securing pin 36 is positioned to contact the posterior portion of head support 16, thus securing head support 16. Once occipital support 14 and head supports 16 have been adjusted to the desired position subsequent applications of the device would not require this adjustment, if applied to the same user, as the adjustments would remain unchanged.

Figure 4A:
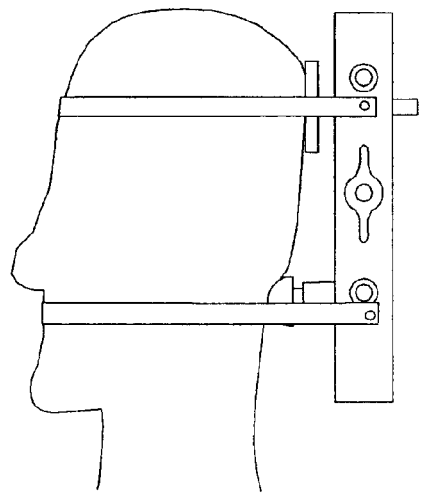
FIG. 4 illustrates a lateral view of my cervical traction device secured on a user of the device.
Figure 4B:
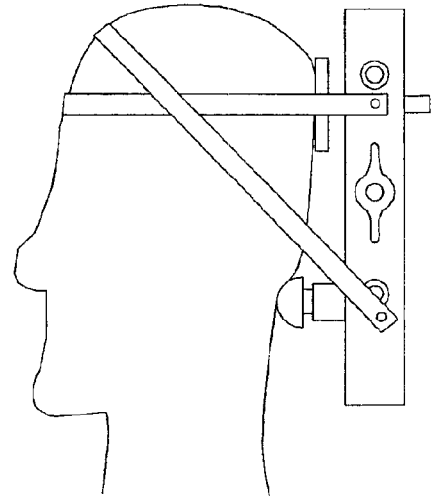
Figure 4C:
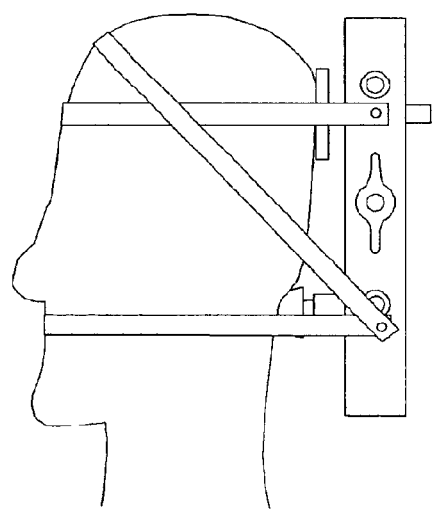

The user of the device would then lay supine on the cervical traction device to secure the device to him/herself. Forehead strap 18 would be secured around the forehead of the user (FIGS. 4a, 4b, and 4c). Attaching maxillary strap 17 around the maxillary area only (FIG. 4a) would allow for a straight alignment of the skull and cervical spine during traction application. Attaching skull strap 19 around the anterior/superior aspect of the skull only (FIG. 4b) would result in upper cervical spine flexion during traction application. Applying both maxillary strap 17 and skull strap 19 simultaneously (FIG. 4c) would result in a combination effect, thus applying a relatively smaller degree of upper cervical spine flexion during traction application.

With the cervical traction device secured properly to the user as illustrated in FIG. 4a, 4b, or 4c, the device would then be attached to a conventional force application device (not shown), such as an overhead door pulley system or other such device, utilizing hook 30.

Conclusions, Ramifications, and Scope of Invention

Thus, the reader will see that the cervical traction device of present invention provides a functional, versatile, and innovative approach to cervical spine traction application that can be utilized by many persons suffering from cervical spine dysfunction. The device allows for elimination of pressure to the temporomandibular joint during traction in an upright position. The device accommodates a variety of positions and angles, allows for a direct longitudinal traction force to be applied to the cervical spine, and can provide direct stretch to suboccipital musculature. The device also accommodates numerous variations in user size and shape, can easily be reapplied by an individual without external assistance, and is easily portable.

While my above option contains many specificities, these should not be construed as limitations on the scope of the invention, but rather as an exemplification of one preferred embodiment there of. Many other variations are possible. For example, supports can have other shapes and sizes, guide and support rods may have differing tension means and adjusting means, and differing adjustment of head and occipital supports are possible that would not change the overall form and function of my present invention.

Thus the scope of the invention should be determined by the appended claims and their legal equivalents, rather than by the examples given.

I claim:

1. A cervical traction device for applying a longitudinal traction to the cervical spine including:

(a) a plurality of main bodies (b) a plurality of guide rods to connect said main bodies (c) an occipital support mounted to the main body (d) a head support mounted to the main body (e) a plurality of straps for securing the head supports and the occipital supports in contact with the user during use of the cervical traction device (f) means for attaching said main bodies to a force application device (g) means for adjusting the position of said occipital support during application of the device (h) a hinge to attach said occipital support to the main body.

2. The cervical traction device of claim 1, further including:

(a) means for adjusting the position of said head support to allow for a plurality of positions dependent upon desired effect.

* * * * *